United States Patent
Tsubata et al.

(10) Patent No.: US 6,758,816 B1
(45) Date of Patent: Jul. 6, 2004

(54) PULSE WAVE DETECTOR

(75) Inventors: Keisuke Tsubata; Hiroshi Odagiri; Chiaki Nakamura; Kazumi Sakumoto; Masataka Shinogi; Takashi Kamimoto, all of Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/558,619

(22) Filed: Apr. 26, 2000

(30) Foreign Application Priority Data

Apr. 28, 1999 (JP) .......................... 11-123072
Dec. 3, 1999 (JP) .......................... 11-344311

(51) Int. Cl.[7] .................................. A61B 8/00
(52) U.S. Cl. ................................... 600/450; 600/459
(58) Field of Search ........................... 600/494, 495, 600/498, 500, 437, 438, 450, 464, 455

(56) References Cited

U.S. PATENT DOCUMENTS

| | | | |
|---|---|---|---|
| 4,086,916 A | | 5/1978 | Freeman et al. ............ 128/2.05 |
| 5,759,157 A | * | 6/1998 | Harada et al. ............... 600/494 |
| 6,036,653 A | * | 3/2000 | Baba et al. .................. 600/500 |
| 6,261,235 B1 | * | 7/2001 | Amano et al. ............... 600/485 |

FOREIGN PATENT DOCUMENTS

| | | |
|---|---|---|
| JP | 01 214335 | 8/1989 |
| JP | 02 116357 | 5/1990 |
| JP | 04067839 | 3/1992 |

\* cited by examiner

*Primary Examiner*—Francis J. Jaworski
*Assistant Examiner*—Maulin Patel
(74) *Attorney, Agent, or Firm*—Adams & Wilks

(57) ABSTRACT

There is provided a pulse wave detector enabling pulse wave detection with reduced power consumption, and prolonged usage time.

Ultrasonic waves having a frequency of 10 MHz are transmitted from a transmitter towards an artery, and reflected waves that have undergone frequency modulation as a result of the Doppler effect of the artery are received by a receiver, pulse waves are extracted by FM detection, and a pulse rate is counted and displayed. Transmission of ultrasonic waves by the transmitter and reception of reflected waves by the receiver are carried intermittently at a frequency of 64 Hz to reduce the power consumption, to enable installation even in a small portable device with low battery capacity such as a watch, and to enable prolonged usage time. The transmitter and receiver have a rectangular shape and are arranged so that a long axis crosses the artery, which means that measurement of pulse waves can be continued without the need to correct positioning even if the artery or a sensor position shifts laterally.

21 Claims, 11 Drawing Sheets

PULSE WAVE DETECTOR

BACKGROUND OF THE INVENTION

1. Technical Field

The present invention relates to a pulse wave detector, and more specifically, to a pulse wave detector for detecting pulse waves by sending and receiving ultrasonic waves to and from an artery.

2. Related Art

Detection of pulse waves caused by blood flow through an artery is widely used in cases such as medical institutions and healthcare administration. This pulse wave detection is also widely used for automatic electronic detection of pulse rate etc., as well as for detecting pulse rate at a specified time by touching an artery with a finger.

As a device for obtaining pulse rate by electronically detecting pulse waves, devices currently exist that have a piezoelectric element arranged on an artery and pulse rate is detected from pressure variations on the skin (positional variations of the skin caused by pressure) accompanying pressure variations inside the artery, or which use ultrasonic waves to detect pulse rate.

Japanese patent laid-open No. Hei. 1-214335 and U.S. Pat. No. 4,086,916, for example, propose use of the Doppler effect caused by blood flow, as a pulse wave detector that uses ultrasonic waves.

FIG. 10 shows the appearance of frequency variations of ultrasonic waves due to this Doppler effect.

If an ultrasonic wave as shown in FIG. 10A having frequency f0 is transmitted from a body surface towards an artery, the transmitted ultrasonic wave is reflected by blood flowing in the artery. If this reflected wave is received by a receiver it is possible to detect variations in the frequency of the reflected wave. Specifically, if the frequency of a received wave is made f1, since the blood flow velocity in the artery is fast in the systolic phase of the heart, the frequency of the reflected wave becomes higher due to the Doppler effect (A part), while conversely the frequency becomes lower than the A part during relaxation of the heart (B part) since the blood flow velocity is lower, as shown in FIG. 10B.

In this way, ultrasonic waves are directed to blood flow in an artery that changes in flow velocity due to beating of the heart, and pulse waves are detected by detecting frequency variation, and it is also possible to detect pulse rate and blood flow velocity.

Also, in German Patent publication No. 3345739 there is proposed a pulse wave detector that uses a plurality of sensors (a plurality of groups of sensors), and FIG. 11 shows the arrangement of a sensor in this type of pulse rate detector. A transmitter 11a and a receiver 21a inside a sensor 19a are rectangular in shape. The longer side of each rectangle is arranged so that it is parallel to blood flow in an artery 2, and so that a line connecting the transmitter 11a and the receiver 21a is orthogonal to the artery 2.

However, with pulse wave detectors for detecting pulse waves using ultrasonic wave Doppler effects, as in the inventions disclosed in Japanese Patent laid-open No. Hei. 1-214335 and U.S. Pat. No. 4,086,916, there is a problem that power consumption is extremely large because ultrasonic waves are used.

As a result, the pulse wave detectors of the related art must be used in an environment such as a hospital or a house where electric power can be adequately supplied, and there is a problem that when they are used in any other environment ultrasonic waves can only be measured for a short time.

Particularly, in the case of a pulse wave detector that is of such a size and weight as to be portable, for instance a pulse wave detector built into a wristwatch, since the battery capacity is limited there is a problem that usage time is made even shorter.

Also, the ultrasonic waves f0 transmitted for pulse wave detection are progressive waves in the order of a few MHz. This means that with a pulse wave detector, such as the invention disclosed in German patent publication No. 3345739, having a long side of a transmitter 11a and receiver 21a arranged parallel to the blood flow of an artery 2, it is necessary to accurately transmit the ultrasonic waves f0 toward the artery 2, and it is difficult to align the position of the sensor 19a. Also, even if the positional alignment is performed accurately, there is a problem that it becomes impossible to measure ultrasonic waves due to positional variations in the artery 2 and the sensor 19 with movement of the wrist 2a.

SUMMARY OF THE INVENTION

The present invention has been conceived in order to solve the above described problems, and a first object of the invention is to provide a pulse wave detector that can detect pulse waves with low power consumption, and which is capable of prolonging usage time.

A second object of the present invention is to provide a pulse wave detector that enables simple alignment of a sensor with an artery, and is capable of carrying out pulse wave detection even when there is wrist movement.

A pulse wave detector of the present invention comprises a transmitter for transmitting ultrasonic waves toward an artery, a receiver for receiving ultrasonic waves transmitted from the transmitter and reflected by blood flowing in the artery, a drive controller for intermittently driving at least one of the transmitter and the receiver, a pulse wave information acquisition unit for acquiring pulse wave information relating to pulse waves from the ultrasonic waves received by the receiver, and an output unit for outputting the pulse wave information acquired by the pulse wave information acquisition unit.

By intermittently driving at least one of the transmitter or the receiver in this way, it is possible to suppress the power consumption to the drive duty cycle. Specifically, a pulse wave detector has low power consumption. For example, by building the pulse wave detector into a watch, it is possible to routinely prolong usage. In this case, it is possible to utilize part or all of an oscillator section used in the watch as the drive controller of the present invention, and in this way an even simpler construction is made possible.

With the pulse wave detector of the present invention, it is possible for the pulse wave information acquisition unit to be provided with a memory for storing pulse wave information, and for the output unit to output the pulse wave information stored in the memory. Specifically, pulse rate information and detection information for specified time sections are stored in the memory in advance, and can be used for medical diagnosis by outputting to an external device such as a medical diagnostic machine.

With the pulse wave detector of the present invention, it is also possible for the pulse wave acquisition unit to acquire a pulse rate from the detection signal as pulse wave information, and for the output unit to output the pulse rate acquired by the pulse wave information acquisition unit. In this way, it is possible to routinely confirm a pulse under normal conditions.

The pulse wave detector of the present invention may also be provided with a display, and it is possible for the pulse wave information acquisition unit to acquire a pulse rate or pulse wave waveform as information relating to a pulse wave from the detection signal, and for the output unit to output the pulse rate or pulse wave waveform acquired by the pulse wave information unit to the display. In this way, by displaying the pulse rate or the pulse wave waveform, it is possible to easily confirm the pulse rate or pulse wave form even during normal day to day activities.

According to another aspect of a pulse wave detector of the present invention, the pulse wave information acquisition unit has a frequency detector for detecting frequency variations of the ultrasonic waves received by the receiver, and pulse wave information is acquired from a detection signal from the frequency detector.

In the pulse wave detector of the present invention, the drive controller intermittently drives both the transmitter and the receiver, and varies the drive timing of the transmitter and the drive means of the receiver. By intermittently driving both the transmitter and the receiver in this way, it is possible to lower power consumption. Also, by making the drive timing of the transmitter and the receiver adjustable, it is possible to adjust the rise times of the transmitter and the receiver to optimum conditions. For example, by starting drive of the receiver a specified time after drive of the transmitter, it is possible to prevent the receiver receiving ultrasonic waves during a time period from start-up of the transmitter until output of ultrasonic waves is stable.

In the pulse wave detector of the present invention, the drive controller intermittently drives both the transmitter and the receiver, and varies the drive times of the transmitter and the drive means of the receiver. By making the time for which the transmitter and the receiver are driven independently adjustable, it is possible, for example, to reduce the drive time of the receiver and reliable receive stable ultrasonic waves. It is also possible to reliably receive all transmitted ultrasonic waves by prolonging the time for which the receiver is driven.

Also, in the pulse wave detector of the present invention, the drive controller varies the drive time and off time for intermittent drive. By making the drive time and the off time adjustable, it is possible to achieve optimum drive while reducing power consumption.

In the pulse wave detector of the present invention, the drive controller intermittently drive at a frequency at least double a maximum assumed heart rate. For example, if the assumed maximum heart rate is 240 beats per minute, at least one of the transmitter and the receiver are intermittently driven at a frequency of 8 Hz or more. Since intermittent drive is always performed at a frequency at least double the frequency to be detected in this way, it is always possible to detect pulse waves in a stable manner. In this case, even if the assumed heart rate is low (an upper limit of 100 beats per minute when at rest) intermittent drive is performed at the same frequency of 8 Hz.

In the pulse wave detector of the present invention, the drive controller performs intermittent drive at a frequency at least double the frequency of the commercial power supply. Specifically, by performing intermittent drive at a frequency of 120 Hz which is at least double the 50 Hz or 60 Hz of a commercial power supply, it is possible to protect against the effects of noise due to the commercial frequency. In this case, by setting the intermittent drive frequency to 128 Hz, it is possible to-possible to divide the oscillating frequency 32 kHz of an oscillator used in a watch to provide the intermittent drive frequency of 128 Hz, making a simple construction possible when the pulse wave detector is implemented in a watch.

In the pulse wave detector of the present invention, the drive controller also performs intermittent drive at a frequency at least double the frequency of a commercial power supply, and at a frequency having an extremely low duty ratio.

A further aspect of the pulse wave detector of the present invention comprises a transmitter for transmitting ultrasonic waves toward an artery, a receiver for receiving ultrasonic waves transmitted from the transmitter and reflected by blood flowing in the artery, a pulse wave information acquisition unit for acquiring pulse wave information relating to pulse waves from the ultrasonic waves received by the receiver, and an output unit for outputting the pulse wave information acquired by the pulse wave information acquisition unit. An ultrasonic wave transmitting surface of the transmitter and an ultrasonic wave receiving surface of the receiver are formed long and narrow in shape having a long axis and a short axis, with the long axis being arranged so as to cross the artery.

A still further aspect of the pulse wave detector of the present invention comprises a transmitter for transmitting ultrasonic waves toward an artery, a receiver for receiving ultrasonic waves transmitted from the transmitter and reflected by blood flowing in the artery, a drive controller for intermittently driving at least one of the transmitter and the receiver, a pulse wave information acquisition unit for acquiring pulse wave information relating to pulse waves from the ultrasonic waves received by the receiver, and an output unit for outputting the pulse wave information acquired by the pulse wave information acquisition unit. An ultrasonic wave transmitting surface of the transmitter and an ultrasonic wave receiving surface of the receiver are formed long and narrow in shape having a long axis and a short axis, with the long axis being arranged so as to cross the artery.

By making the transmitting surface of the transmitter and the receiving surface of the receiver long and narrow in shape in this way, with a long axis and a short axis, the transmitter and the receiver are positioned over an artery even if the artery slides in a lateral range of the circumference of the wrist, which means that there is no need to correct the position of the transmitter and the receiver, and it is possible to continue measuring pulse waves.

Also, since the transmitter and the receiver are arranged so that the long axis intersects the arterial blood flow direction, it is possible to transmit ultrasonic waves towards the artery and to receive reflected waves without specially correcting a sensor position, even if the sensor deviates from the artery along the circumference of the wrist, as long as the amount of deviation is within the range of the long axis.

Further, it is possible to affix a strap to a user's wrist without a user paying particularly attention to placement of the transmitter and receiver over the artery.

DESCRIPTION OF THE DRAWINGS

A preferred form of the present invention is illustrated in the accompanying drawings in which.

DETAILED DESCRIPTION OF PREFERRED EMBODIMENTS

Preferred embodiments of a pulse wave detector of the present invention will now be described in detail, with reference to FIG. 1 to FIG. 9.

With a pulse wave detector of a first embodiment, ultrasonic waves f0 having a frequency of 10 MHz are transmitted from a body surface of a transmitter 11 towards an artery 2, and reflected waves f1 that have undergone frequency modulation as a result of the Doppler effect of blood flow, which is the subject of reflection (subject of measurement) are received by a receiver 21. Pulse waves are extracted by FM detection of these received waves, and a pulse rate is counted and displayed.

Transmission of ultrasonic waves f0 by the transmitter 11 and reception of reflected waves f1 by the receiver 21 are carried intermittently at a frequency of 64 Hz.

By intermittently driving the transmitter 11 and the receiver 21 it is possible to reduce the power consumption, installation is possible even in a small portable device with low battery capacity such as a watch, and prolonged usage time is enabled.

The transmitter 11 and receiver 21 of the pulse wave detector of this embodiment have a rectangular shape and are arranged side by side so that a long axis crosses the artery 2. In this way, there is no need to correct the position of the transmitter 11 and the receiver 21, even if the artery 2 or a sensor position shifts laterally due to movement of the wrist 2a, measurement of pulse waves can be continued and it is possible to accurately detect pulse wave information.

The first embodiment will now be described in greater detail.

Figure 1:
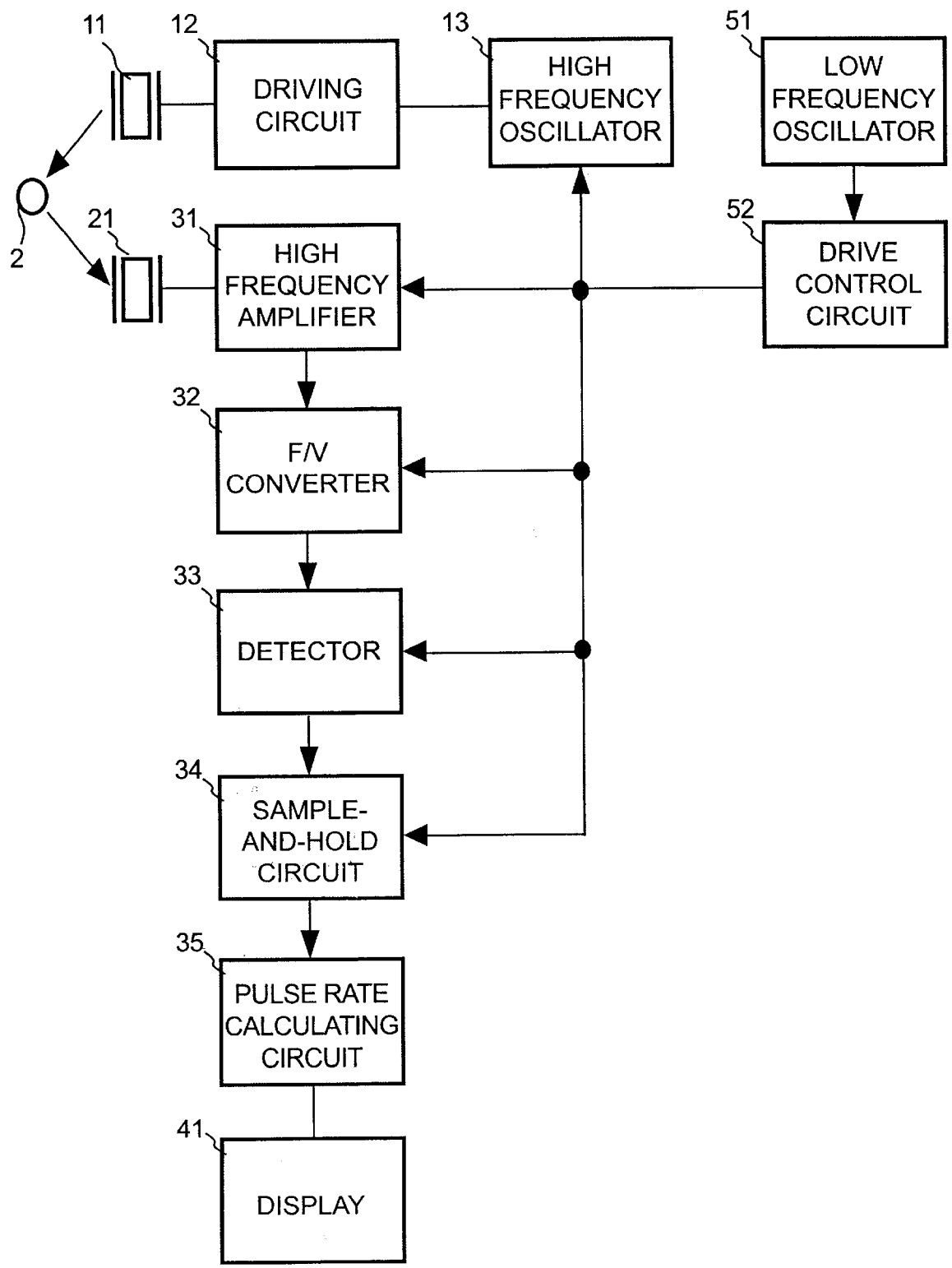
FIG. 1 is a block diagram of a pulse wave detector of a first embodiment of the present invention.

FIG. 1 shows the structure of the pulse wave detector of the first embodiment.

As shown in FIG. 1, the pulse wave detector is provided with a transmitter 11, a driving circuit 12 and a high frequency oscillator 13 for transmitting ultrasonic waves towards an artery 2.

The pulse wave detector also has a receiver 21, a high frequency amplifier 31, an F/V converter 32, a detector 33, a sample-and-hold circuit 34, a pulse rate calculating circuit 35, and a display 41 for receiving ultrasonic waves reflected by blood flow of the artery 2 and obtaining a pulse rate.

A low frequency oscillator 51 and a drive control circuit 52 are also provided in the pulse wave detector.

The low frequency oscillator 51 generates a signal oscillating at 32 KHz. The drive control circuit 52 divides the oscillation signal from the low frequency oscillator 51 by 500 and supplies the result as a 64 Khz intermittent drive signal to the high frequency oscillator 13, the high frequency amplifier 31, the F/V converter 32, the detector 33 and the sample-and-hold circuit 34.

The high frequency oscillator 13 generates a high frequency signal of 10 MHz, and outputs this 10 MHz signal intermittently at 64 KHz using the intermittent drive signal supplied from the drive control circuit 52. The intermittently output high frequency signal is supplied to the driving circuit 12.

The driving circuit 12 amplifies the high frequency signal intermittently supplied from the high frequency oscillator 13 to a power used for output and supplies it to the transmitter 11 to cause ultrasonic waves f0 to be transmitted from the transmitter 11.

Ultrasonic waves f0 transmitted from the transmitter 11 are reflected while being subjected to frequency modulation by blood flow in the artery 2, and these reflected ultrasonic waves f1 are received by the receiver 21 and supplied to the high frequency amplifier 31.

The high frequency amplifier 31 amplifies the reflected waves f1 and supplies to result to the F/V converter 32.

The F/V converter 32 outputs a voltage corresponding to the frequency, using voltage gain variation corresponding to the frequency value.

The detector 33 outputs a voltage corresponding to an envelope by amplitude detection.

A voltage when the intermittent drive signal is ON is also output when the intermittent drive signal is OFF, by the sample-and-hold circuit 34, and this voltage is aligned with the 64 Hz intermittent drive signal supplied from the drive control circuit 52.

The pulse rate calculating circuit 35 calculates a pulse rate from the sample and hold signal.

The display 41 digitally displays the pulse rate, and comprises a display section and a drive section.

The operation of this embodiment having the above described construction will now be described.

First of all, the principal of detecting pulse waves from frequency modulation of ultrasonic waves transmitted towards the artery 2 due to the Doppler effect of the blood flow velocity will be described.

Blood flowing in the artery 2 is subject to variations in blood flow velocity according to the systolic phase and diastolic phase of the heart. As a result, the frequency of transmitted ultrasonic waves varies due to the Doppler effect when reflected by the blood flow.

The frequency f1 of the reflected waves at this time can be obtained from the following equation (1), where frequency of the ultrasonic waves is f0, blood flow velocity is v, the speed of sound in the body is c, the angle at which the ultrasonic waves are incident for the blood flow rate is θ.

$$f1 = f0\,(1 + 2v \times \cos\theta/c) \quad \text{(Equation 1)}$$

The frequency of the ultrasonic waves varies in the range f0–f1 depending on reflection, and this deviation is obtained from the following equation (2).

$$df = f1 - f0 = f0 \times 2v \times \cos\theta/c \qquad \text{(Equation 2)}$$

Accordingly, if the respective values are made c=155 m/s, v=0.3 m/s, and f0=9.5, for example, the frequency deviation becomes 3.8 kHz.

In equation 2, the blood flow velocity v varies with pulse rate, and the frequency deviation df varies in the range from about 2 KHz to 4 KHz.

In this embodiment, this variation in the frequency deviation df is detected using a method of demodulating the frequency modulation, so as to detect pulse waves.

FIG. 2 show output waveforms for each section of the pulse wave detector.

Figure 2A:
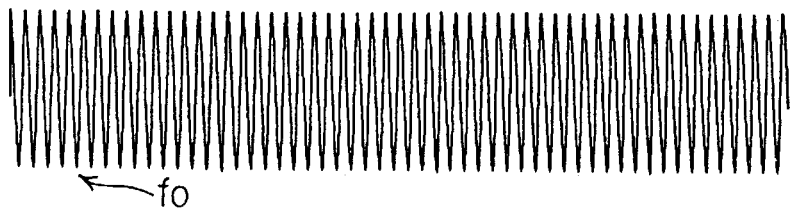
FIG. 2 are drawings illustrating the display of an output waveform at each section of the pulse wave detector of the first embodiment.

The high frequency oscillator 13 internally generates the high frequency signal f0 of frequency 10 MHz, as shown in FIG. 2A.

Figure 2B:
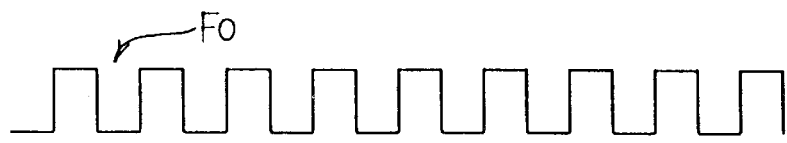

A low frequency signal of 32 kHz oscillating in the low frequency oscillator 51 is divided to 64 Hz by the drive control circuit 52, and the intermittent drive signal F0 shown in FIG. 2B is supplied to the high frequency oscillator 13 and the high frequency amplifier 31 etc.

Figure 2C:
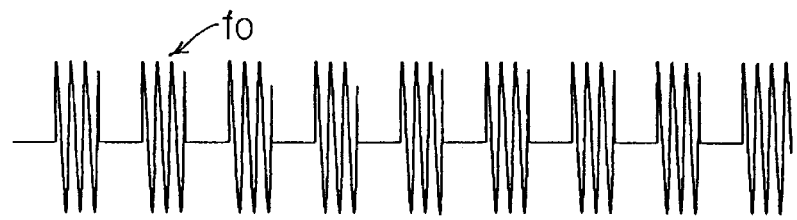

The high frequency oscillator 13 intermittently supplies the 10 MHz high frequency signal f0 to the driving circuit 12 at the period of this 64 Hz intermittent drive signal F0, as shown in FIG. 2C.

In the driving circuit 12, the output power of the intermittently supplied high frequency signal f0 is amplified, and supplied to the transmitter 11 constituted by a piezoelectric element, to transmit ultrasonic waves f0 similar to the high frequency waves shown in FIG. 2C toward the artery 2.

Figure 2D:
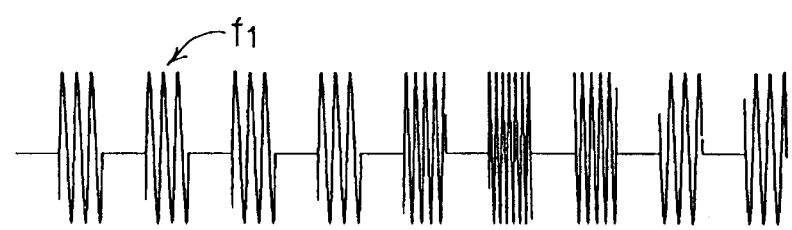

The supplied ultrasonic waves f0 are subjected to frequency modulation due to the Doppler effect when they are reflected by the blood flowing in the artery 2, and the frequency modulated reflected waves f1 are intermittently received by the receiver 21 at the period of 64 kHz, as shown in FIG. 2D.

The reflected waves f1 are amplified in the high frequency amplifier 31 and then supplied to the F/V converter 32.

Figure 2E:
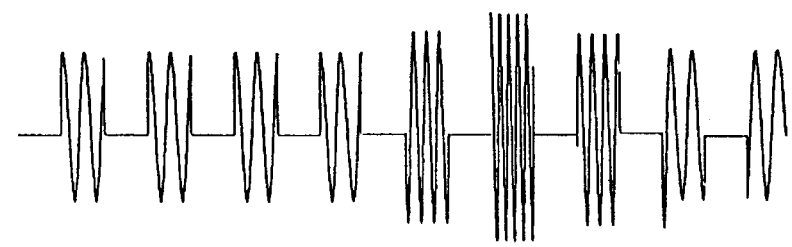
Figure 2F:

Frequency variations of the amplified reflected waves f1 are converted to voltage variations, or more specifically amplitude variations, by the F/V converter 32, as shown in FIG. 2E. By subjecting these amplitude variations to amplitude detection in the detector 33, they are converted to a pulse signal having voltage values corresponding to the envelope, as shown in FIG. 2F.

Figure 2G:

This pulse signal is then supplied as a continuous signal, as shown in FIG. 2G, to the pulse rate calculating circuit 35 by the sample-and-hold circuit 34.

In this embodiment, the frequency of intermittently driving ultrasonic waves to be transmitted is set to F0=64 Hz. This frequency F0 is larger than 8 Hz, being double the period of pulse waves in the case of the assumed maximum heart rate of 240 beats per minute, namely 4 Hz, which means that even if transmission and reception of ultrasonic waves are carried out intermittently at the frequency F0=64 Hz, it is possible to detect pulse waves with sufficient stability.

A pulse wave is generated by the pulse rate calculating circuit 35 when, for example, a comparison value is exceeded by a comparison circuit, and the time interval of this pulse wave is measured a specified number of times (for example, 3 times, 5 times, seven times, 10 times, etc.) so as to obtain a pulse rate N for one minute from a mean time T of each measurement period from the following equation (3).

$$N = 60/T \qquad \text{(Equation 3)}$$

The present invention is not limited to obtaining the pulse rate from the mean time T of the pulse period, and it also possible, for example, to detect the number of pulses generated within a specified period t (for example, 10 seconds) and obtain the pulse rate for one minute from the following equation 4.

$$N = w \times (60/t) \qquad \text{(Equation 4)}$$

The pulse rate calculating circuit 35 supplies the obtained pulse rate N and a pulse signal generated in correspondence with each pulse to the display 41.

The supplied pulse rate N is digitally displayed on a liquid crystal display by the display 41, and the existence of a pulse is also indicated by carrying out flashing green display in response to supplied pulse signals. By watching this flashing green display, a user can visually recognize their own pulse waves.

It is also possible to recognize the existence of a pulse audibly by outputting a pulse tone in response to supplied pulse signals.

FIG. 3 shows the situation when pulse waves are detected by a pulse wave detector built into a watch.

Figure 3A:
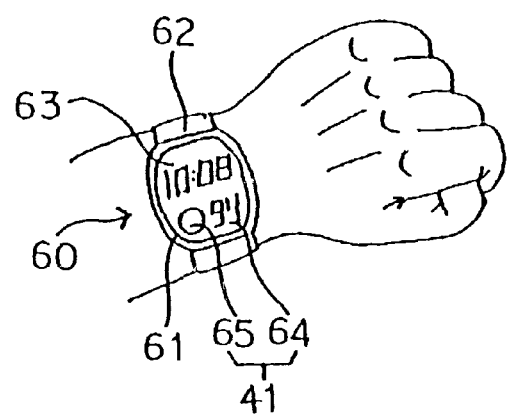
FIG. 3 are drawings illustrating display of conditions for detecting pulse waves using the pulse wave detector of the first embodiment built into a watch.
Figure 3B:
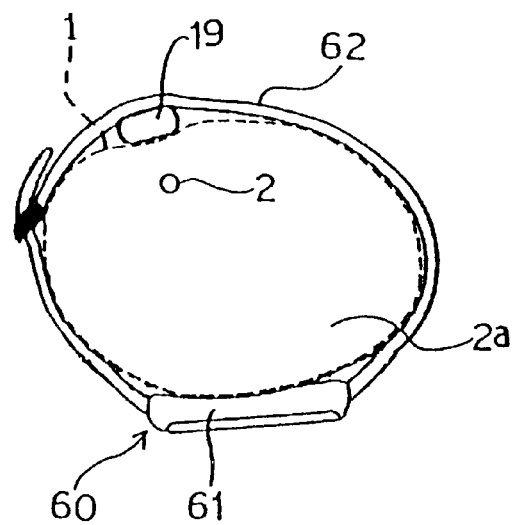

As shown in FIG. 3, the pulse wave detector 60 (watch) is provided with a watch body 61 and a strap 62, and a sensor 19 is attached to the inner side of the strap 62. The watch 60 is the same as a normal watch, and the watch body 61 is placed on the back of the hand and attached to the left (or right) wrist 2a. At this time, the sensor 19 is positioned over the radial artery in such a way that the sensor 19 can be adjusted by moving in the length direction of the strap 62, as shown in FIG. 3B.

Figure 3C:
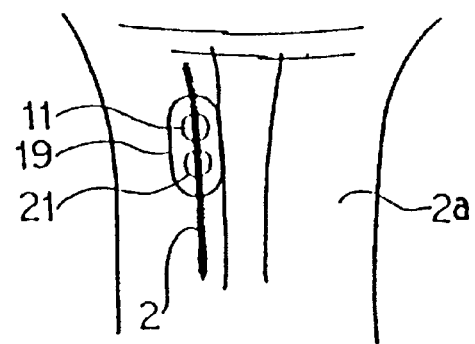

The transmitter 11 and the receiver 21 are aligned on the sensor 19 in a direction orthogonal to the length direction of the strap 62 and along the radial artery 2, as shown in FIG. 3C, with the transmitter 11 being arranged more towards the hand and the receiver 21 being arranged more towards the elbow. It is also possible for the positions at which the transmitter 11 and the receiver 21 are arranged to be reversed.

Besides drive sections for the movement of the watch, etc., the driving circuit 12, high frequency oscillator 13, high frequency amplifier 31, F/V converter 32, detector 33, sample-and-hold circuit 34, pulse rate calculating circuit 35, display 41, low frequency oscillator 51 and drive control circuit 52 are also arranged in the watch body 61. Since the low frequency oscillator 51 has a common oscillation frequency, it can also be used as the drive circuit used for the watch functions.

The driving circuit 12 of the watch body 61 and the high frequency amplifier 31 are connected to the sensor 19 using wiring, not shown in the drawing, built into the inside of the strap 62.

A display surface (dial) of the watch body 61 comprises a watch display section 63 for displaying the time (or the date or the day of the week) and a display 41. The display 41 comprises a pulse rate display section 64 for displaying the pulse rate N, and a pulse display section 65 that flashes green in response to each pulse, as shown in FIG. 3A.

It is also possible to vary the flashing color of the pulse display section 65 according to the pulse rate. For example, it is possible to make the pulse display section 65 flash yellow at a pulse rate below 69, flash blue at a pulse rate between 70 and 90, flash green at a pulse rate between 91 and 110, flash orange at a pule rate between 111 and 130, and flash red at a pulse rate above 131. In this way, since the color that the pulse display section 65 flashes is varied depending on the pulse rate, it is easy to distinguish the current pulse conditions.

As described above, according to the first embodiment, since ultrasonic waves transmitted from the transmitter 11 are normally output continuously, and signal processing, such as amplification of reflected waves f0 received by the receiver 21 is not constantly carried out, so as to transmit and receive (including signal processing such as amplification) intermittently at frequency F0, it is possible to reduce power consumption to the drive duty cycle part.

Accordingly, even with a small portable device with limited battery capacity, such the watch shown in FIG. 3, it is possible to prolong the usage time by having low power consumption.

Next, a second embodiment of the present invention will be described.

Figure 4:
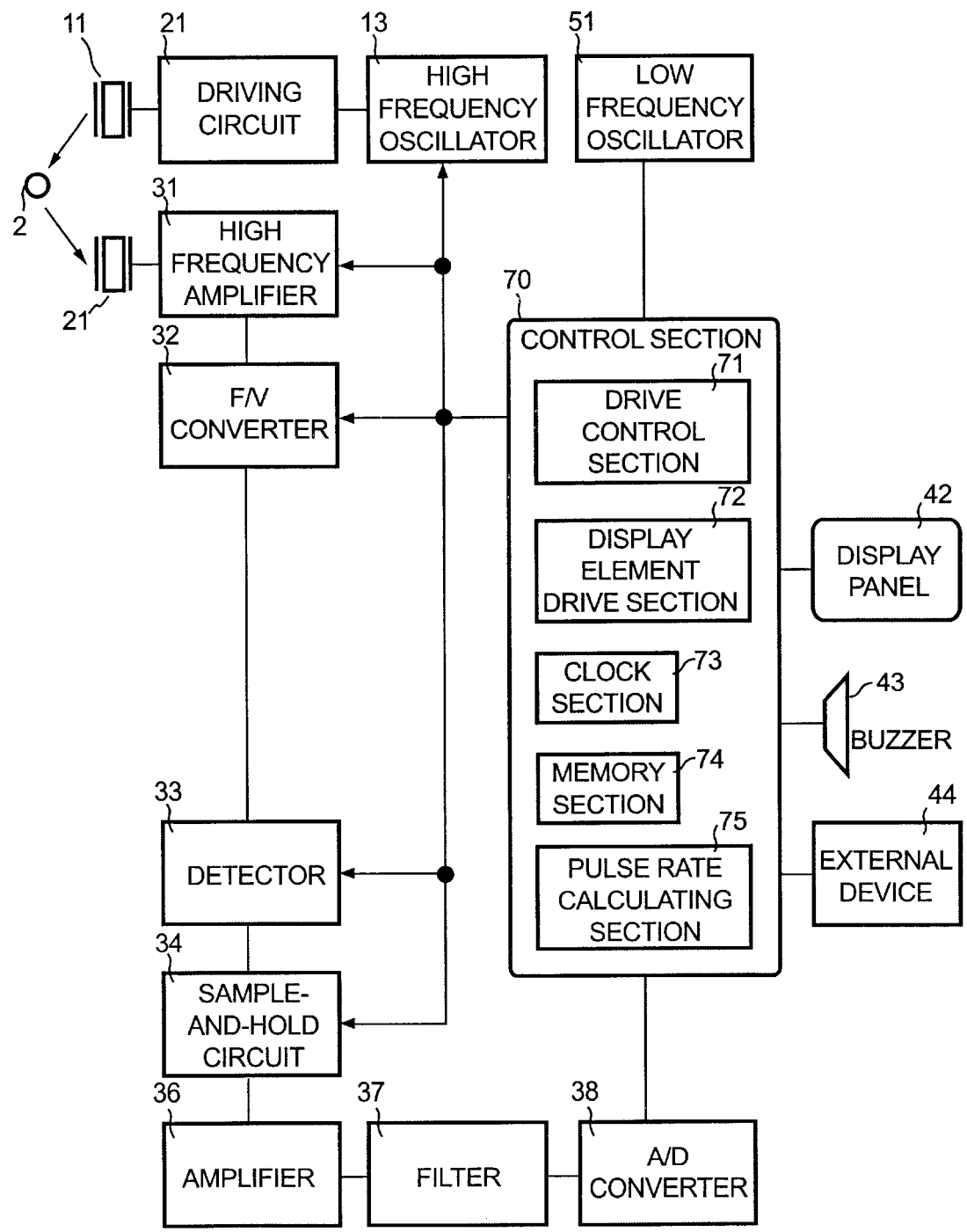
FIG. 4 is a block diagram of a pulse wave detector of a second embodiment of the present invention.

FIG. 4 shows the construction of the pulse wave detector of the second embodiment. Parts that are the same as in the first embodiment have the same reference numerals attached thereto, and description will be omitted.

With this second embodiment, as shown in FIG. 4, a control section 70 for carrying out digital processing is provided in place of the drive control circuit 52, the pulse rate calculating circuit 35 and the display 41.

An amplifier circuit 36, filter circuit 37 and A/D converter 38 are additionally arranged between the sample-and-hold circuit 34 and the control section 70.

Also, a display panel 42 (equivalent to the display section of the display 41) and a buzzer 43 are connected to the control section 70 as output devices. It is also possible to connect various external devices 44, such as a personal computer or medical diagnostic equipment to the control section 70.

The control section 70 is mainly constructed as a micro computer system provided with a CPU (central processor unit), ROM (Read Only Memory), RAM (Random Access Memory) and other parts, and these components provide an interface section (not shown) for connecting together a drive controller 71 (equivalent to the drive controller 52), a display element drive controller 72 for controlling display of the display panel 42, a watch section 73, a memory 74, a pulse rate calculating section (equivalent to the pulse rate calculating circuit 35) and an external device 44.

It is possible to use various storage medium for magnetically, electrically or optically storing data, such as DRAM, SRAM, EEPROM or a hard disc, etc. in the memory 74, and although the storage capacity of the memory 74 is arbitrary, a storage device capable of accumulating at least one hour to one day's worth of pulse wave information, preferably up to a week's pulse wave information, and more preferably a month's worth of information, is used.

With the pulse wave detector of the second embodiment, similarly to the first embodiment, pulse waves are detected from variations in frequency of ultrasonic waves, a signal output from the sample-and-hold circuit 34 is amplified by the amplifier circuit 36, and after removing a commercial noise component using the filter circuit 37, the signal is converted to a digital signal comprising pulse wave information by the A/D converter 38 and supplied to the control section 70.

If digital pulse wave information is supplied, the control section 70 calculates pulse rate N from the previously described equations (3) and (4) in the pulse rate calculating section 75, and displays the pulse rate N and a flashing green display corresponding to the pulse rate on the display panel 42 using the display element drive controller 72.

The control section 70 also outputs a pulse tone from the 43 in synchronism with the flashing green display corresponding to the pulse, if a buzzer switch, not shown in the drawings, is switched on.

The control section 70 also has pulse wave information (waveforms) to be supplied stored in advance in the memory 74. In this way, by accumulating pulse information for a specified period in the memory 74 in advance, it is possible, in the future, to connect an external device 44 to the pulse wave detector, and output the pulse wave information accumulated in the memory 74 for use in health care diagnosis etc.

In this way, in a diagnostic device for health care (an external device), pulse wave information for a long period of time is acquired and it is possible to carry out diagnosis more accurately, from a medicinal point of view, under the normal day to day circumstances of the user. For example, it is possible to evaluate whether or not the user is in a psychologically tense state or in relaxed state by studying pulse variations. It is also possible to study pulse wave rhythm, pulse size, or the rate at which pulses rise (whether they are fast or slow) etc.

A third embodiment will now be described.

In this third embodiment, pulse waves are acquired by using decay of ultrasonic waves caused by blood flow amount in an artery.

First of all, the theory and outline of the pulse wave detector of this embodiment will be described with reference to FIG. 5.

If the amount of blood flow in an artery varies, the transfer constant when the ultrasonic waves are propagated varies. This is thought to be because blood flow amount and blood density vary depending on the artery, and the attenuation factor of ultrasonic waves varies.

Figure 5A:
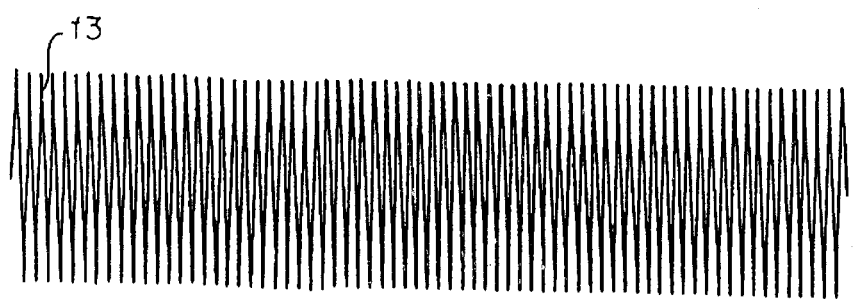
FIG. 5 are drawings illustrating the principal and outline of pulse wave detection in a third embodiment of a pulse wave detector of the present invention.
Figure 5B:
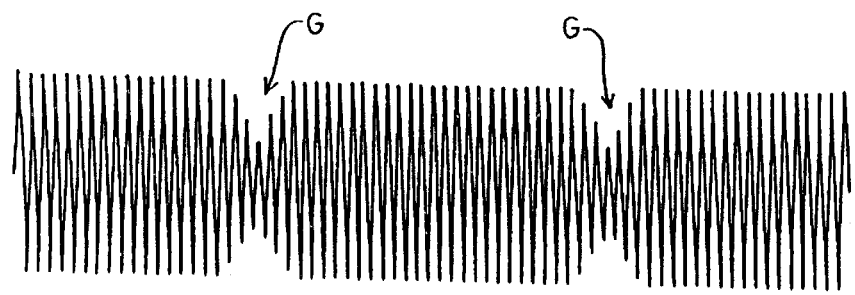
Figure 5C:

In this embodiment, based on the above theory, the ultrasonic waves shown in FIG. 5A are transmitted from the transmitter 11 towards the artery. The frequency f3 of the ultrasonic waves at this time is smaller than the frequency f0=10 MHz of ultrasonic waves that are the object of frequency modulation by the blood flow, and a value of f3=32 kHz is used. These ultrasonic waves are propagated (reflected) by the arterial flow in the artery, while being subject to attenuation, ultrasonic waves (propagated waves) attenuated in accordance with pulses, as shown in FIG. 5B (portions shown by arrows G), are received by the receiver 21, and the pulse wave waveform (waveform information) H shown in FIG. 5C is obtained by performing amplitude detection on the received ultrasonic waves.

In this embodiment, based on this sort of principal, transmission of ultrasonic waves from the transmitter 11 and amplitude detection of ultrasonic waves received by the receiver 21 are performed intermittently, as in the first embodiment, thus making the power consumption small.

Figure 6:
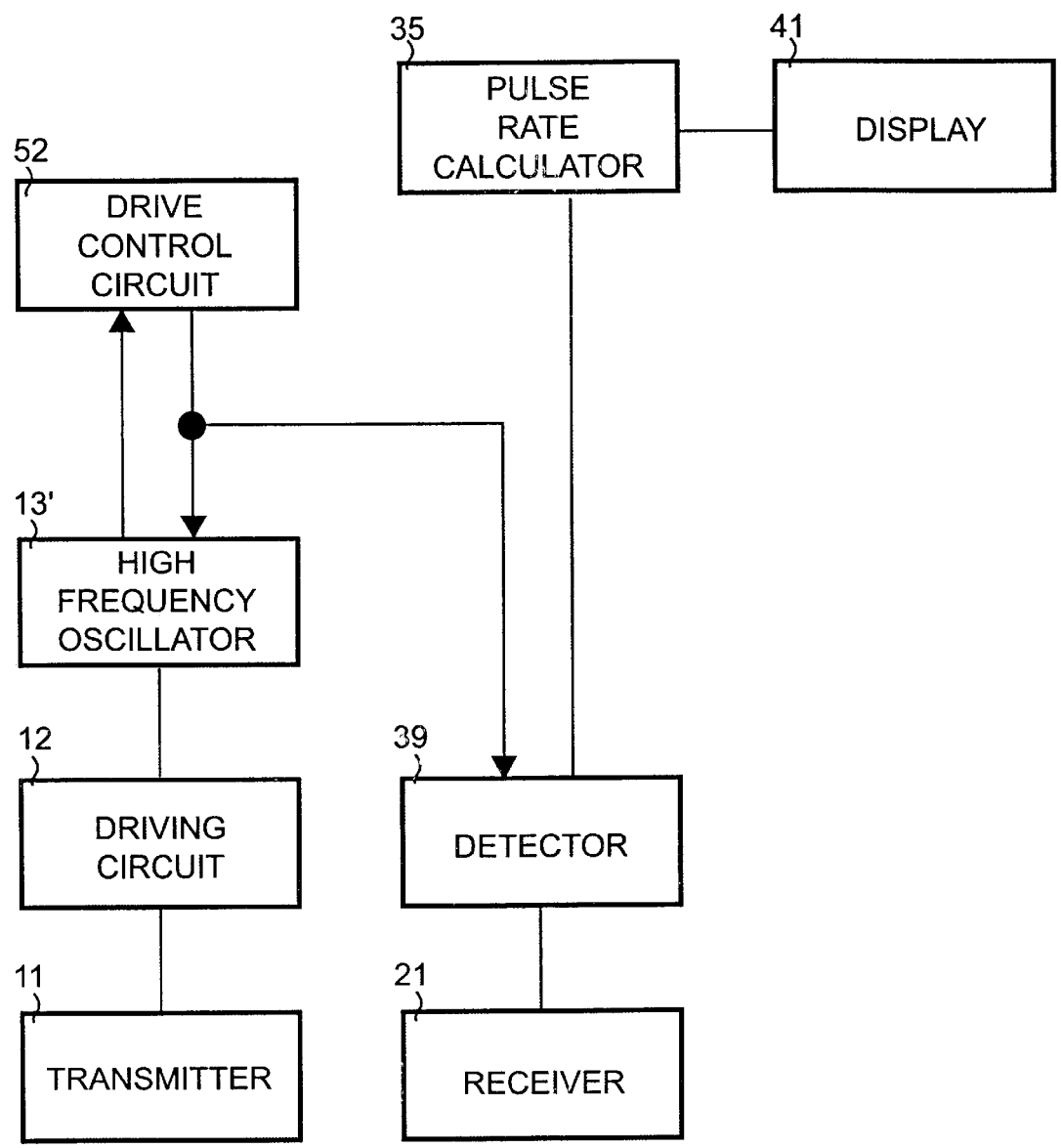
FIG. 6 is a block diagram of a pulse wave detector of a first embodiment of the present invention.

FIG. 6 shows the configuration of a pulse wave detector of the third embodiment. In the description of the third embodiment, parts that are the same as those in the first embodiment have the same reference numerals attached thereto, and description of those parts will be omitted.

A high frequency oscillator 13' of the pulse wave detector of the third embodiment is also provided with the function of the low frequency oscillator 51 of the first embodiment, and generates high frequency signal of frequency f3=32 kHz and supplies it to the drive control circuit 52.

The drive control circuit 52 divides the supplied oscillation signal by 500 to give a 64 kHz intermittent drive signal, in the same way as in the first embodiment, and supplies the intermittent drive signal to the high frequency oscillator 13' and the detection section 30.

The high frequency oscillator 13' outputs the high frequency of 32 kHz intermittently at 64 Hz, using the intermittent drive signal F0 supplied from the drive control circuit 52.

This intermittently output high frequency f3 is amplified by the driving circuit 12 to a power suitable for output and then supplied to the transmitter 11 in order to transmit ultrasonic waves A from the transmitter 11.

The oscillation frequency f3 of the high frequency oscillator 13' is not limited to 32 kHz, and it is possible to transmit ultrasonic waves of any arbitrary frequency. It is possible to select the frequency used in a range of 20–50 kHz and preferably in the range 30–40 kHz. Also, in the case of using an oscillation frequency m other than that of a watch, it is possible to use the same frequency m as the oscillation frequency.

As shown in FIG. 6, ultrasonic waves A are attenuated by the blood flow while being propagated, and these propagated waves F are received by the receiver 21 and then subjected to amplitude detection by the detection section 39 to acquire pulse wave information.

Detection and signal processing in the detection section 39 is also carried out intermittently in response with the intermittent drive signal F0 supplied from the drive control circuit 52, which enables reduced power consumption.

The pulse rate N is calculated by the pulse rate calculating circuit 35 from the supplied pulse wave information after amplitude detection, similarly to the first embodiment, and the pulse rate N is displayed on the display 41.

As has been described above, in the third embodiment, since the amount of attenuation (amount of amplitude variation) of ultrasonic waves propagated by the artery is large compared to the small value, namely 2–4 kHz, of frequency deviation caused by the Doppler effect, detection can be carried out easily.

Also, since there is no variation in blood flow amount (blood flow velocity) itself even. if there is body movement, which means that since it is highly unlikely that body movement will constitute noise with respect to the amplitude variations of the ultrasonic waves, it is possible to carry out pulse wave detection that is hardly affected by body movement.

A fourth embodiment of the present invention will now be described.

The fourth embodiment has a modification relating to the shape and arrangement of the transmitter 11 and the receiver 21 inside the sensor 19 in FIG. 3C of the first embodiment.

This embodiment has a similar construction to the pulse wave detector for detecting pulse wave information in FIG. 1 and FIG. 4 to FIG. 6, but is different in the shape and arrangement of the transmitter 11 and receiver 21 inside the sensor 19 when ultrasonic waves, being pulse wave information, are detected.

Figure 7:
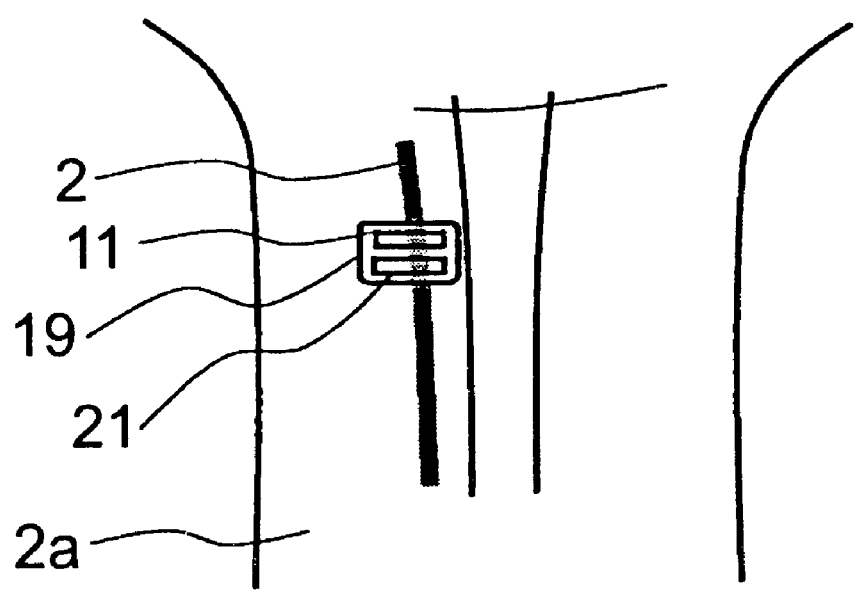
FIG. 7 is a drawing showing a sensor of a fourth embodiment of the present invention.

FIG. 7 is a drawing showing a sensor of the fourth embodiment of the present invention. FIGS. 8A and 8B show the external appearance of the pulse wave detector (watch) of the fourth embodiment.

As shown in FIG. 7 and FIGS. 8A–8B, the transmitter 11 and the receiver 21 inside the sensor 19 are formed so that the shape of a surface coming into contact with the wrist surface (ultrasonic waves transmission surface, ultrasonic waves reception surface) is rectangular. The transmitter 11 and the receiver 21 are arranged so that the longer edges of the rectangles are parallel to the circumference of the wrist 2a and cross the artery 2.

As shown in FIG. 8A–8B, the rectangular shaped transmitter 11 and receiver 21 are arranged in the longitudinal direction of the strap 62 so that the longer edges cross the artery 2.

Figure 8:
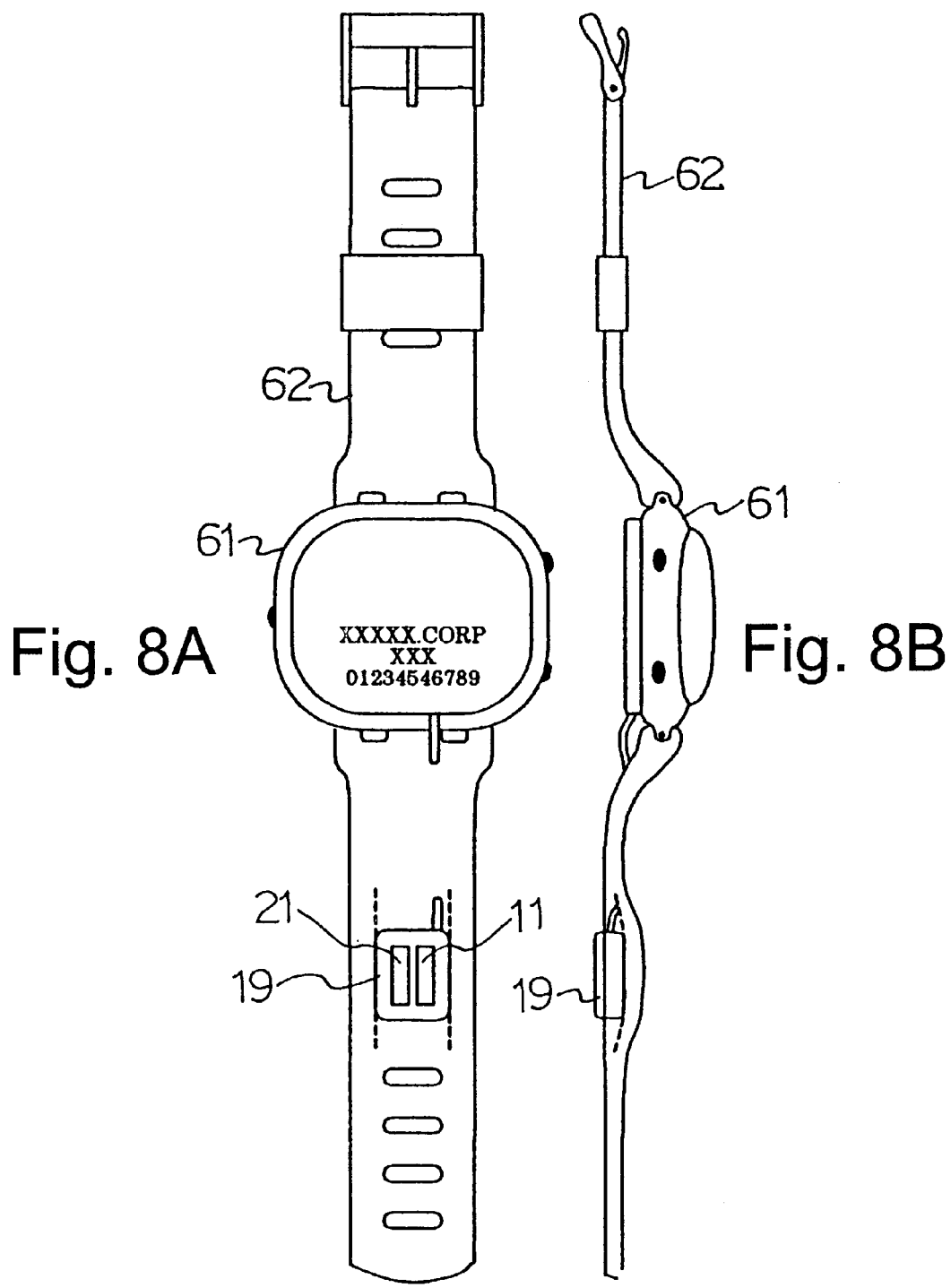
FIG. 8 are drawings showing the external appearance of a pulse wave detector (watch) of the fourth embodiment.

With the fourth embodiment, as will be understood more clearly from FIG. 7 and FIG. 8, by making the shape of the transmitter 11 and the receiver 21 rectangular, the range on the circumference of the wrist 2a to which ultrasonic waves can be transmitted and received is increased, which means that even if the position of the artery 2 or the sensor 19 slips around the circumference of the wrist 2a it is possible to continue measurement of pulse waves without the need to correct the position of the sensor 19 as long as it is within the transmit and receive range. Also, a user can wear the belt on the wrist 2a without being particularly aware that the sensor 19 is above the artery 2.

In the fourth embodiment, the shape of the transmitter 11 and the receiver 21 is rectangular, but this is only one example and the present invention is not limited in this respect. For example, any shape is possible as long as the shape has a long axis and a short axis, such as a diamond shape or a strip, etc., as well as a shape such as an ellipse having a long diameter and a short diameter. Also, at least parts of the transmitter 11 and the receiver 21 that come into contact with the surface of the wrist 2a are shaped having a long axis or a long diameter running along in the circumference of the wrist 2a.

The case has been described where a sensor of the intermittently driven pulse wave detector of FIG. 1, FIG. 4 and FIG. 6 is used as the sensor of the fourth embodiment, but it is also possible to adopt a sensor format for a pulse wave detector that is not intermittently driven (continuous drive), in which the transmitter 11 transmits ultrasonic waves f0 to the artery 2 in response to a continuously supplied high frequency signal and reflected waves f1 subjected to frequency modulation while being reflected by the blood flow of the artery 2 are received by the receiver 21.

Figure 9:
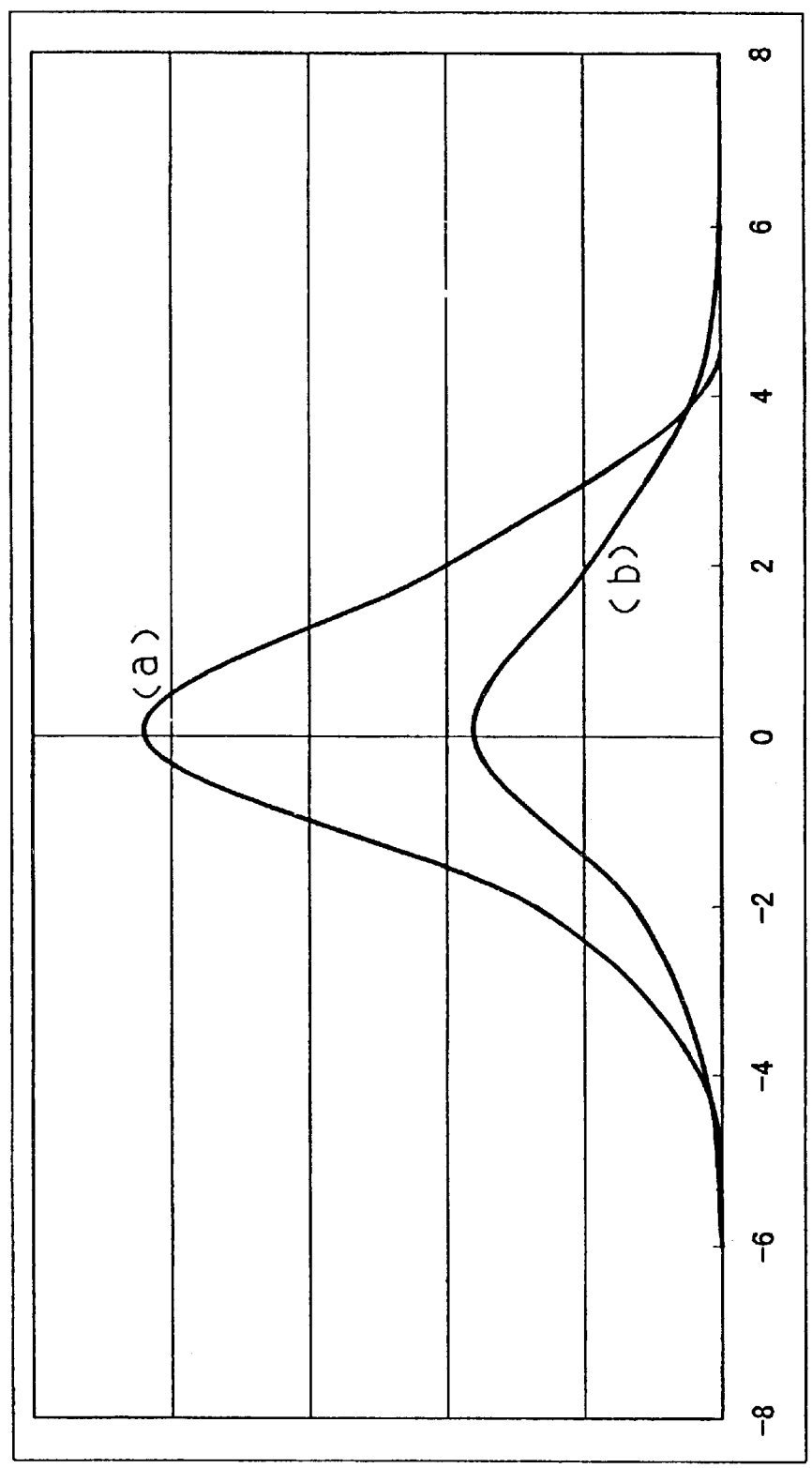
FIG. 9 is a drawing showing differences in detection accuracy attributable to shape and arrangement of the receiver and transmitter inside the sensor.
Figure 10:
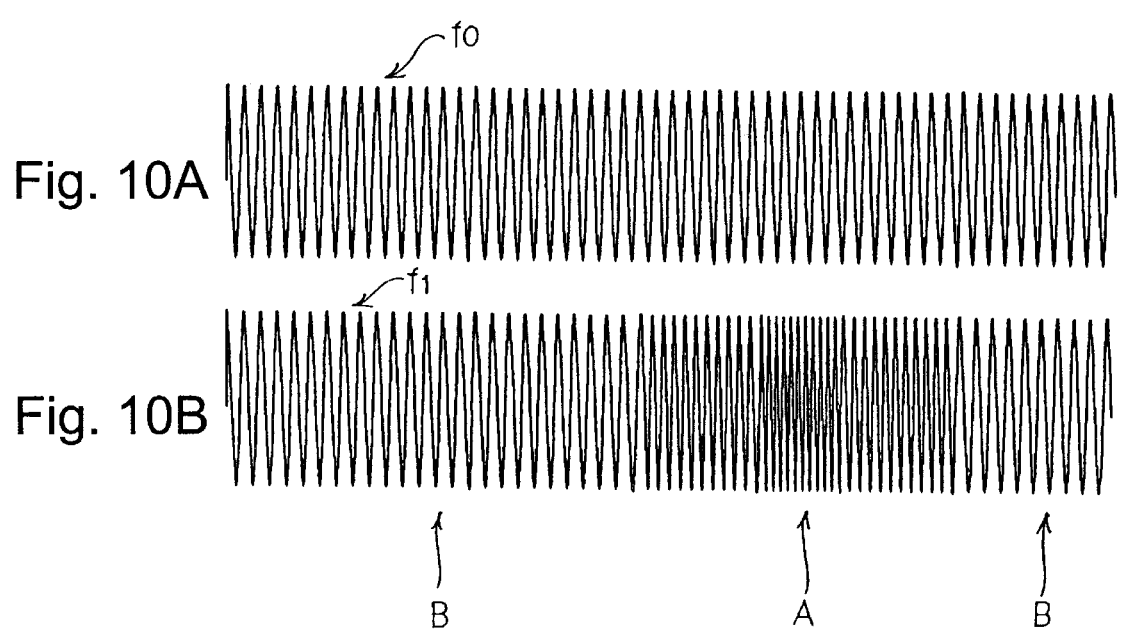
FIG. 10 are drawings for describing display of appearance of variations in frequency of ultrasonic waves due to the Doppler effect.
Figure 11:
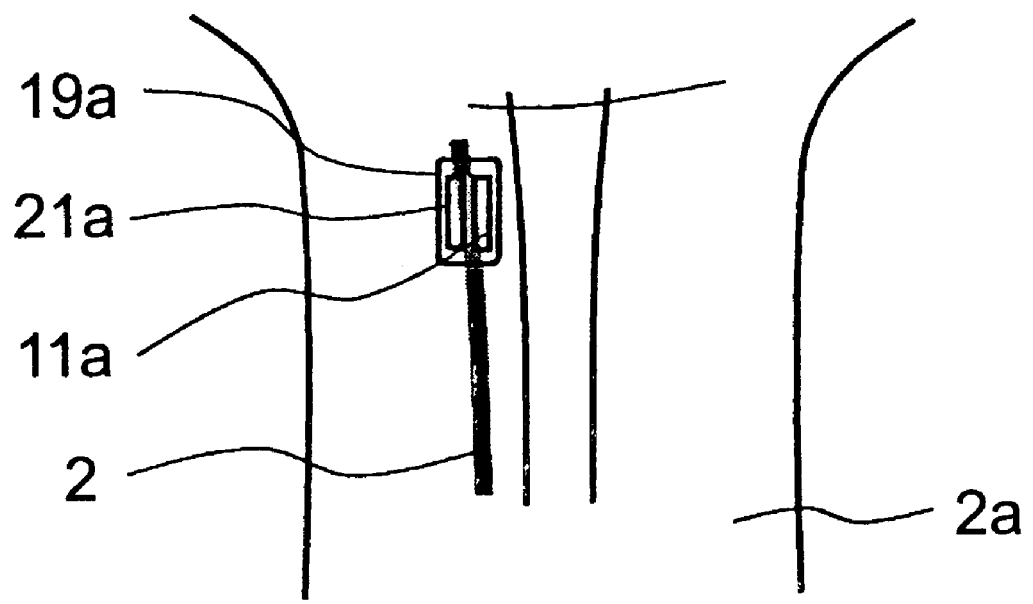
FIG. 11 is a drawing showing arrangement of a sensor in a pulse wave detector of the related art.

FIG. 9 is a drawing showing deviation in detection accuracy with shape of the transmitter 11 and receiver 21 of the sensor 19. FIG. 9A shows detection accuracy in the case where the shape of the transmitter 11 and receiver 21 are rectangular, as described in the fourth embodiment, while FIG. 9b shows detection accuracy for the case when the longer side of each rectangle is arranged so that it is parallel to blood flow in an artery 2, and so that a line connecting the transmitter 11a and the receiver 21a is orthogonal to the artery 2, as shown in FIG. 11.

The vertical axis in FIG. 9 represents output of the pulse wave detector, and detection accuracy of pulse wave information is high going up the scale. The horizontal axis represents the extent of positional displacement of the artery 2 from the center of the sensor 19 or the sensor 19a, with the center being 0.

For the same range of positional displacement of the artery 2 from the center of the sensor 19, if FIG. 9A and FIG. 9B are compared, it will be understood that the fourth embodiment is more capable of accurate detection of pulse waves with transmission and reception of ultrasonic waves over a wide range on the circumference of the wrist.

Therefore, by making the shape of the transmitter 11 and receiver 21 rectangular or substantially rectangular, as in the fourth embodiment, and arranging the transmitter 11 and receiver 21 so as to cross the blood flow direction of the artery 2, it is possible to carry out pulse wave detection with strong positional cohesion between the sensor and the artery, and with good accuracy.

A description has been give of the preferred embodiments of the present invention above, but the present invention is not limited to these embodiments, and various modifications are possible within the spirit and scope of the invention as defined by the appended claims.

For example, in the described embodiments both transmission of ultrasonic waves and reception of reflected waves (including propagated waves) is carried out intermittently using the intermittent drive signal F0, but the present invention can also reduce power consumption compared to the related art even if only one of transmission or reception is carried out intermittently.

It is also possible to adjust the output timing for high frequency f0 and the process timing for reflected waves f1 in sections from the high frequency amplifier 31 to the sample-and-hold circuit 34, by means of intermittent drive using the high frequency oscillator 13.

By making it possible to adjust the transmission side and reception side intermittent drive timing in this way, it is possible to adjust the times for which transmission and reception are active to the optimum conditions. For example, by starting the receive side after a fixed delay from the activation of the transmission side, it is possible-to stop reception on the receive side for the period of time from when transmission is started until output of ultrasonic waves becomes stable.

It is also possible to independently adjust the transmit side drive timing and the receive side drive timing in the pulse wave detector. For example, by shortening the time for which the transmit side is active, it is possible to reliably receive stable ultrasonic waves. Conversely, by prolonging the time for which the receive side is active, it is possible to reliably receive all ultrasonic waves transmitted.

It is also possible, in the pulse wave detector, to adjust a ratio of the time for which intermittent drive is on to the time intermittent drive is off so as to enable optimum operation while reducing power consumption. The ratio of the on time to the off time can be adjusted for both the transmit side and the receive side, or for only one of the transmit side or the receive side.

In the embodiments described above, the frequency F0 of the intermittent drive signal is 64 Hz, but it is possible to perform intermittent drive at any frequency greater than double the expected maximum pulse rate. For example, the frequency F0 of the intermittent drive signal can be a frequency of 8 Hz or higher. If F0 is made 8 Hz, the drive control circuit 52 divides the 32 kHz oscillation signal supplied from the low frequency oscillator 51 or high frequency oscillator 13' by 4000.

The frequency of the intermittent drive signal can also be 128 Hz. This makes it difficult for noise due to commercial frequencies to have any effect, because the intermittent drive signal is at least double the frequency of a commercial power supply. In this case, the drive control circuit 52 divides the 32 kHz oscillation signal by 250.

It is further possible for the intermittent drive signal to have a frequency of at least double the commercial power supply frequency and to have an extremely low duty cycle.

In the above described first embodiment, as shown in FIG. 1, the intermittent drive signal F0 output from the drive control circuit 52 is supplied to the high frequency oscillator 13 and it also possible to supply the intermittent drive signal to the driving circuit 12. In this case, the high frequency oscillator 13 continuously supplies a high frequency f0 of 10 MHz to the driving circuit 12, and the driving circuit 12 carries out amplification in response to the intermittent drive signal F0 and supplies output to the transmitter 11.

In the above described embodiments, description has been given with respect to detecting pulse wave information with a radial artery as an example, but it is also possible to transmit and receive ultrasonic waves to and from other arteries, such as the brachial artery, femoral artery, common carotid artery, ulnar artery, forward common carotid artery, backward common carotid artery, the dorsal artery of the foot or the popliteal artery (popliteal fossa artery).

In this case, depending on the artery position where the pulse wave detector is attached, it is preferable to position the sensor 19 over the artery using medical tape instead of the strap 62. Also, when a special sensor 19 is attached above the artery using medical tape and measurement of pulse information is carried out, by transmitting the detected data to a receiver built into a watch or the like pulse information measured at parts of the user other than the wrist can still be viewed on the display section of the watch.

With to the pulse wave detector of the present invention, since at least one of a transmitter or a receiver are driven intermittently, it is possible to detect pulse waves with reduced power consumption, and to prolong the usage time.

The pulse wave detector of the present invention also makes it possible to simply line up the sensor with the artery and to continuously carry out pulse wave detection even if the wrist is moved, because the transmitter and receiver are shaped having a long axis and a short axis, with the long axis being arranged to cross the artery.

What is claimed is:

1. A pulse wave detector, comprising:

transmission means for transmitting ultrasonic waves toward an artery of a living body;

receive means for receiving ultrasonic waves transmitted from the transmission means and reflected by blood flowing in the artery;

drive control means for intermittently driving at least one of the transmission means and the receive means;

pulse wave information acquisition means for acquiring pulse wave information from ultrasonic waves received by the receive means; and output means for outputting the pulse wave information acquired by the pulse wave information acquisition means.

2. The pulse wave detector according to of claim 1; wherein the pulse wave information acquisition means includes frequency detection means for detecting frequency variations of the ultrasonic waves received by the receiving means and producing therefrom a detection signal constituting the pulse wave information.

3. A pulse wave detector according to claim 1; wherein the pulse wave information acquisition means includes amplitude detection means for detecting amplitude variations of ultrasonic waves received by the receiving means and producing therefrom a detection signal constituting the pulse wave information.

4. A pulse wave detector as in any one of claims 1–3; wherein the drive control means includes means for intermittently driving the transmission means and the receiving means and for varying the drive timing of the transmission means and the receiving means.

5. A pulse wave detector as in any one of claims 1–3; wherein the drive control means includes means for intermittently driving the transmission means and the receiving means and for varying the drive duration of the transmission means and the receiving means.

6. A pulse wave detector as in any one of claims 1–3; wherein the drive control means includes means for varying intermittent drive duration and intermittent drive stop time of at least one of the transmission means and the receiving means.

7. A pulse wave detector as in any one of claims 1–3; further comprising calculating means for calculating a pulse rate in accordance with pulse wave information from the output means; wherein the drive control means includes means for intermittently driving at least one of the transmission means and the receiving means at a frequency which is at least twice as that of a preselected maximum pulse rate.

8. A pulse wave detector as in any one of claims 1–3; further comprising a power supply for supplying power to the pulse wave detector; wherein the drive control means includes means for intermittently driving at least one of the transmission means and the receiving means at a frequency which is at least twice as that of the power supply.

9. A pulse wave detector as in any one of claims 1–3; further comprising a power supply for supplying power to the pulse wave detector; wherein the drive control means includes means for intermittently driving at least one of the transmission means and the receiving means at a low duty cycle and at a frequency which is at least twice that of the power supply.

10. A pulse wave detector comprising:
transmission means having a transmitting surface for transmitting ultrasonic waves toward an artery of a living body while the transmitting surface is disposed to cross the artery;
receiving means having a receiving surface for receiving ultrasonic waves transmitted from the transmission means and reflected by blood flowing in the artery while the receiving surface is disposed to cross the artery;
pulse wave information acquisition means for acquiring pulse wave information from ultrasonic waves received by the receiving means; and
output means for outputting pulse wave information acquired by the pulse wave information acquisition means.

11. A pulse wave detector comprising:
transmission means having a transmitting surface for transmitting ultrasonic waves toward an artery of a living body while the transmitting surface is disposed to cross the artery;
receiving means having a receiving surface for receiving ultrasonic waves transmitted from the transmission means and reflected by blood flowing in the artery while the receiving surface is disposed to cross the artery;
drive control means for intermittently driving at least one of the transmission means and the receiving means;
pulse wave information acquisition means for acquiring pulse wave information from ultrasonic waves received by the receiving means; and
output means for outputting pulse wave information acquired by the pulse wave information acquisition means.

12. A pulse wave detector according to claim 1; wherein the artery is selected from the group consisting of a radial artery, a brachial artery, a femoral artery, a common carotid artery, an ulnar artery, a forward common carotid artery, a backward common carotid artery, a dorsal artery of a foot of the living body and a popliteal artery.

13. A pulse wave detector according to claim 1; wherein the transmission means comprises a transmitter having an elongated shape having a pair of opposed long edges disposed to cross the artery while ultrasonic waves are transmitted toward the artery; and wherein the receiving means comprises a receiver having an elongated shape having a pair of opposed long edges disposed to cross the artery while receiving ultrasonic waves transmitted from the transmitter and reflected by blood flowing in the artery.

14. A pulse wave detector according to claim 10; wherein the transmitting surface of the transmission means has a first edge and a second edge having a length longer that of the first edge; and wherein the second edge of the transmitting surface is disposed to cross the artery during transmission of ultrasonic waves toward the artery.

15. A pulse wave detector according to claim 14; wherein the receiving surface of the receiving means has a first edge and a second edge having a length longer than that of the first edge; and wherein the second edge of the receiving surface is disposed to cross the artery while the receiving means receives ultrasonic waves transmitted from the transmission means and reflected by blood flowing in the artery.

16. A pulse wave detector according to claim 11; wherein the transmitting surface of the transmission means has a first edge and a second edge having a length longer than that of the first edge; and wherein the second edge of the transmitting surface is disposed to cross the artery during transmission of ultrasonic waves toward the artery.

17. A pulse wave detector according to claim 16; wherein the receiving surface of the receiving means has a first edge and a second edge having a length longer than that of the first edge; and wherein the second edge of the receiving surface is disposed to cross the artery while the receiving means receives ultrasonic waves transmitted from the transmission means and reflected by blood flowing in the artery.

18. A pulse wave detector comprising: a transmitter for transmitting ultrasonic waves toward an artery of a living body; a receiver for receiving ultrasonic waves transmitted from the transmitter and reflected by blood flowing in the artery; a drive control circuit for intermittently driving the transmitter and the receiver; and a pulse wave information extractor for extracting pulse wave information from ultrasonic waves received by the receiver.

19. A pulse wave detector according to claim 18; wherein the artery is selected from the group consisting of a radial artery, a brachial artery, a femoral artery, a common carotid artery, an ulnar artery, a forward common carotid artery, a backward common carotid artery, a dorsal artery of a foot of the living body and a popliteal artery.

20. A pulse wave detector according to claim 18; wherein the transmitter has an elongated shape having a pair of opposed long edges disposed to cross the artery while the transmitter transmits ultrasonic waves toward the artery.

21. A pulse wave detector according to claim 20; wherein the receiver has an elongated shape having a pair of opposed long edges disposed to cross the artery while the receiver receives ultrasonic waves transmitted from the transmitter and reflected by blood flowing in the artery.

* * * * *